United States Patent
Li

(10) Patent No.: US 12,279,930 B2
(45) Date of Patent: Apr. 22, 2025

(54) HEARING PROTECTION METHOD CAPABLE OF BLOCKING EXTERNAL HIGH-SOUND-PRESSURE-LEVEL ENERGY

(71) Applicant: Shenzhen Dancing Future Technology Ltd., Shenzhen (CN)

(72) Inventor: Xinyu Li, Shenzhen (CN)

(73) Assignee: SHENZHEN DANCING FUTURE TECHNOLOGY LTD., Shenzhen (CN)

( * ) Notice: Subject to any disclaimer, the term of this patent is extended or adjusted under 35 U.S.C. 154(b) by 364 days.

(21) Appl. No.: 18/059,970

(22) Filed: Nov. 29, 2022

(65) Prior Publication Data
US 2023/0201041 A1 Jun. 29, 2023

(30) Foreign Application Priority Data
Dec. 23, 2021 (CN) .......................... 202111589540.4

(51) Int. Cl.
*A61F 11/14* (2006.01)
*G10K 11/178* (2006.01)
*H04R 1/10* (2006.01)

(52) U.S. Cl.
CPC ...... *A61F 11/145* (2022.01); *G10K 11/17879* (2018.01); *H04R 1/1083* (2013.01);
(Continued)

(58) Field of Classification Search
CPC .......................... H04R 1/1083; H04R 1/1091; H04R 2225/41; H04R 25/43; H04R 25/48;
(Continued)

(56) References Cited

U.S. PATENT DOCUMENTS 10,347,236 B1 * 7/2019 Bastyr .............. G10K 11/17823
10,586,523 B1 * 3/2020 Kohler ............. G10K 11/17854
(Continued)

FOREIGN PATENT DOCUMENTS

CN 106101929 A 11/2016
CN 110274379 A 9/2019
(Continued)

OTHER PUBLICATIONS

Office Action in Japanese Patent Application No. 2022-188882, mailed Jan. 9, 2024, 8 pages.
(Continued)

*Primary Examiner* — Lun-See Lao
(74) *Attorney, Agent, or Firm* — Astute IP Law Group

(57) ABSTRACT

The present disclosure provides a hearing protection method capable of blocking external high-sound-pressure-level energy, including: a second sound pressure energy threshold being greater than a first sound pressure energy threshold; when an external sound energy value is greater than the first sound pressure energy threshold and is less than the second sound pressure energy threshold, enabling a preset active noise cancellation function; and when the external sound energy value is greater than the second sound pressure energy threshold, disabling the preset active noise cancellation function, and blocking high-sound-pressure-level energy by means of passive noise cancellation. The present disclosure can block the external high-sound-pressure-level energy.

7 Claims, 2 Drawing Sheets

(52) U.S. Cl.
CPC .............. *G10K 2210/1081* (2013.01); *G10K 2210/3039* (2013.01); *H04R 2460/01* (2013.01)

(58) Field of Classification Search
CPC .. H04R 25/554; H04R 25/556; H04R 25/607; H04R 1/005; H04R 1/1041; H04R 19/00; H04R 2460/01; H04R 5/033; G10K 11/17823; G10K 11/17837; G10K 11/17861; G10K 11/17879; G10K 2210/1081; G10K 2210/3039; G10K 2210/3056; G10L 25/69; H04L 12/10; H04L 12/40045; H04L 2012/40273
USPC ........................ 381/56–58, 94.1–94.5, 312
See application file for complete search history.

(56) References Cited

U.S. PATENT DOCUMENTS

| | | | | |
|---|---|---|---|---|
| 2014/0169601 | A1* | 6/2014 | Pedersen | H04R 25/48 381/316 |
| 2016/0302029 | A1* | 10/2016 | Broadley | H04M 1/6058 |
| 2019/0385583 | A1* | 12/2019 | Muggleton | G10K 11/17881 |
| 2020/0357377 | A1* | 11/2020 | Bastyr | G10K 11/17817 |

FOREIGN PATENT DOCUMENTS

| | | |
|---|---|---|
| CN | 111510822 A | 8/2020 |
| CN | 112312258 A | 2/2021 |
| CN | 113099340 A | 7/2021 |
| JP | H06130966 A | 5/1994 |
| JP | H06282283 A | 10/1994 |
| JP | H06314097 A | 11/1994 |
| JP | H086572 A | 1/1996 |
| JP | 2007216787 A | 8/2007 |
| JP | 2014033303 A | 2/2014 |
| JP | 2018506906 A | 3/2018 |
| WO | 2016059878 A1 | 4/2016 |

OTHER PUBLICATIONS

Office Action for Chinese Patent Application No. 202111589540.4, mailed on Sep. 11, 2024, 14 pages.

Office Action for Chinese Patent Application No. 20211589540.4, mailed on Feb. 17, 2025, 8 pages.

* cited by examiner

HEARING PROTECTION METHOD CAPABLE OF BLOCKING EXTERNAL HIGH-SOUND-PRESSURE-LEVEL ENERGY

CROSS REFERENCE TO RELATED APPLICATIONS

The present application claims the benefit of Chinese Patent Application No. 202111589540.4 filed on Dec. 23, 2021, the contents of which are incorporated herein by reference in their entirety.

FIELD OF TECHNOLOGY

The present disclosure relates to a noise cancellation processing method for an audio device, in particular to a hearing protection method capable of blocking external high-sound-pressure-level energy.

BACKGROUND

Hearing protection is very important in daily life. In many cases, when people realize that they need to protect their hearing, they already have problems with hearing. However, hearing impairment is basically irreversible. For young people, noise is the most serious factor causing hearing loss. Meanwhile, headphones have a great impact on hearing of people.

Referring to FIG. 1, according to existing data, the higher the decibel value of a sound is, the greater the damage to the human ears is. Seeing the following table for human ear's tolerance to noise:

| Sound pressure (dBA) | Duration (min) |
| --- | --- |
| 80 | 480 |
| 83 | 240 |
| 86 | 120 |
| 89 | 60 |
| 92 | 30 |
| 95 | 15 |
| 98 | 7.5 |
| 101 | 3.75 |

In the prior art, ambient noise is generally reduced by means of active noise cancellation (ANC), and users may listen to music at a lower volume, thereby protecting their hearing. However, there are several exceptions:

Firstly, when the ANC is enabled and there is a high sound pressure level, the sound pressure level of a microphone with the ANC is already saturated, causing a distorted signal to be superimposed into the ear, such that the noise is not reduced and higher energy that impairs hearing is generated.

Secondly, when the ANC is disabled, part of external high-sound-pressure-level energy is blocked by only passive noise cancellation, such that the ANC function cannot be effectively used.

In addition, when the ANC is in a pass-through mode, a system will amplify the high-sound-pressure-level energy, which leads to increase of sound energy in the ear, thus causing impairment.

SUMMARY

In view of the deficiencies in the prior art, the present disclosure provides a hearing protection method capable of protecting hearing when high-sound-pressure-level energy suddenly occurs outside to block the external high-sound-pressure-level energy, so as to solve the technical problem.

To solve the above technical problem, the present disclosure adopts the following technical solution:

A hearing protection method capable of blocking external high-sound-pressure-level energy, including the following steps: Step S1: presetting a first sound pressure energy threshold and a second sound pressure energy threshold, the second sound pressure energy threshold being greater than the first sound pressure energy threshold; Step S2: obtaining an external sound energy value; Step S3: comparing the external sound energy value with the first sound pressure energy threshold and the second sound pressure energy threshold, when the external sound energy value is greater than the first sound pressure energy threshold and is less than the second sound pressure energy threshold, performing Step S4, and when the external sound energy value is greater than the second sound pressure energy threshold, performing Step S5; Step S4: enabling a preset active noise cancellation function to reduce high-sound-pressure-level energy; and Step S5: disabling the preset active noise cancellation function, and blocking the high-sound-pressure-level energy by means of passive noise cancellation.

Preferably, in the Step S1, a sound pressure energy level of a feed forward microphone (FF MIC), equivalent to a sound pressure level (SPL) of 80 dBA at an eardrum of a user, is taken as the first sound pressure energy threshold.

Preferably, in the Step S1, a high sound pressure energy level, about to be saturated, of the FF MIC obtained by a laboratory test is taken as the second sound pressure energy threshold.

Preferably, in the Step S2, the external sound energy value is obtained by the FF MIC or a Talk MIC.

Preferably, in the Step S2, the process of obtaining the external sound energy value includes: converting the change of an external sound signal acquired in real time by the FF MIC or the Talk MIC into an audio data stream, and calculating the audio data stream by means of an A-weighted digital system to obtain the current external sound energy value.

Preferably, the transfer function of the A-weighted digital system is converted into a digital filter by means of bilinear transformation.

Preferably, a virtual switch is correspondingly provided in the hearing protection method and is arranged in a preset application (App), the Step S1 to the Step S5 are performed when the virtual switch is turned on, and the Step S1 to the Step S5 are not performed when the virtual switch is turned off.

In the hearing protection method capable of blocking the external high-sound-pressure-level energy provided by the present disclosure, the hearing protection function is realized by monitoring the external high-sound-pressure-level energy in real time and taking intervention measures. In the specific process, the external high-sound-pressure-level energy is monitored in real time and is compared with the preset first sound pressure energy threshold and second sound pressure energy threshold; when the high-sound-pressure-level energy exceeds the preset first sound pressure energy threshold, a system will enable the active noise cancellation (ANC) function to protect hearing; and when the high-sound-pressure-level energy exceeds the preset second sound pressure energy threshold, the system will disable the ANC function to protect hearing. Compared with the prior art, the present disclosure can block the external high-sound-pressure-level energy, and can effectively protect hearing when the high-sound-pressure-level energy suddenly occurs outside, thereby better meeting application requirements.

DESCRIPTION OF THE EMBODIMENTS

The present disclosure is described in more detail below in conjunction with the accompanying drawings and the embodiments.

Figure 1:
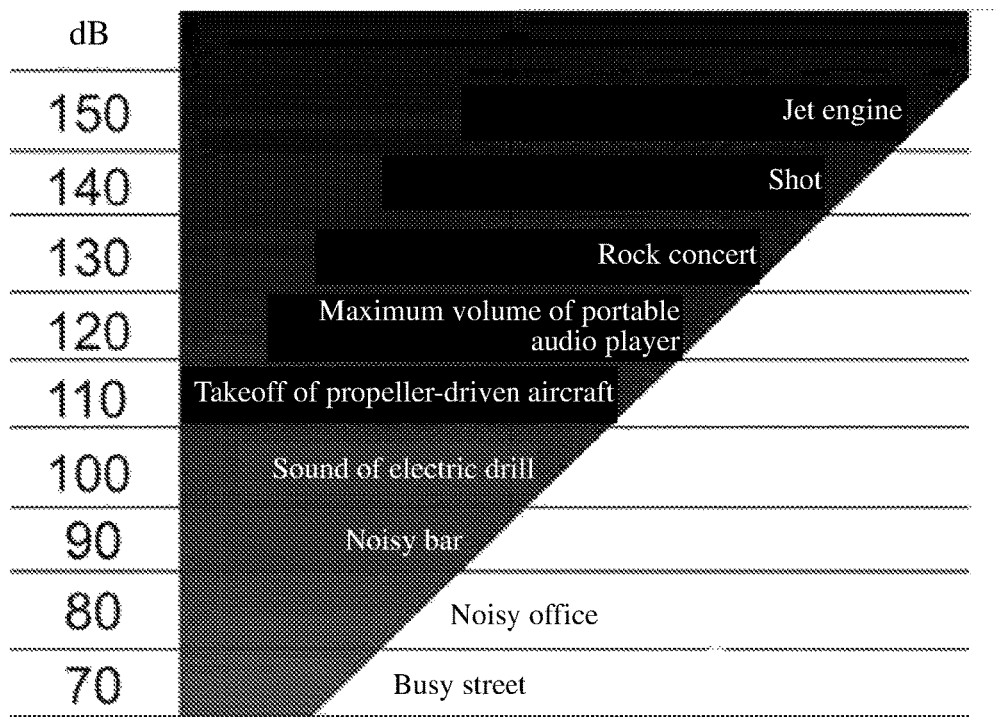
FIG. 1 is a schematic diagram of an environment corresponding to a decibel value of a sound in existing data.
Figure 2:
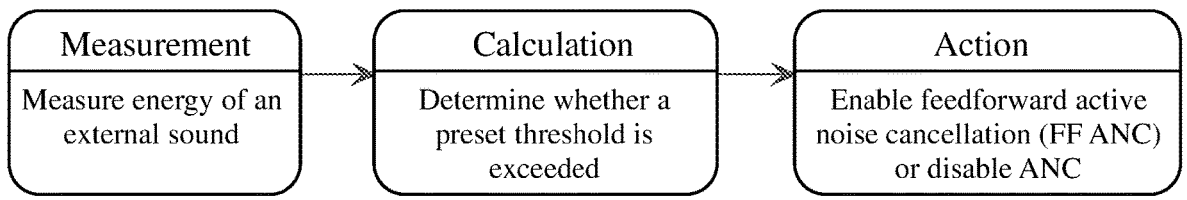
FIG. 2 is a flowchart of a hearing protection method in the present disclosure.

The present disclosure discloses a hearing protection method capable of blocking external high-sound-pressure-level energy. Referring to FIG. 2, the method includes the following steps:

Step S1: presetting a first sound pressure energy threshold and a second sound pressure energy threshold, the second sound pressure energy threshold being greater than the first sound pressure energy threshold;

Step S2: obtaining an external sound energy value;

Step S3: comparing the external sound energy value with the first sound pressure energy threshold and the second sound pressure energy threshold, when the external sound energy value is greater than the first sound pressure energy threshold and is less than the second sound pressure energy threshold, performing Step S4, and when the external sound energy value is greater than the second sound pressure energy threshold, performing Step S5;

Step S4: enabling a preset active noise cancellation function to reduce high-sound-pressure-level energy; and Step S5: disabling the preset active noise cancellation function, and blocking the high-sound-pressure-level energy by means of passive noise cancellation.

In the above method, the hearing protection function is realized by monitoring the external high-sound-pressure-level energy in real time and taking intervention measures. In the specific process, the external high-sound-pressure-level energy is monitored in real time and is compared with the preset first sound pressure energy threshold and second sound pressure energy threshold; when the high-sound-pressure-level energy exceeds the preset first sound pressure energy threshold, a system will enable the active noise cancellation (ANC) function to protect hearing; and when the high-sound-pressure-level energy exceeds the preset second sound pressure energy threshold, the system will disable the ANC function to protect hearing. Compared with the prior art, the present disclosure can block the external high-sound-pressure-level energy, and can effectively protect hearing when the high-sound-pressure-level energy suddenly occurs outside, thereby better meeting application requirements.

As a preferred embodiment, in the Step S1, a sound pressure energy level of a feed forward microphone (FF MIC), equivalent to a sound pressure level (SPL) of 80 dBA at an eardrum of a user, is taken as the first sound pressure energy threshold. In the Step S1, a high sound pressure energy level, about to be saturated, of the FF MIC obtained by a laboratory test is taken as the second sound pressure energy threshold.

In the Step S2 of this embodiment, the external sound energy value is obtained by the FF MIC or a Talk MIC. Specifically, in the Step S2, the process of obtaining the external sound energy value includes: converting the change of an external sound signal acquired in real time by the FF MIC or the Talk MIC into an audio data stream, and calculating the audio data stream by means of an A-weighted digital system to obtain the current external sound energy value.

One specific embodiment is provided below as a further explanation.

Embodiment 1

In this embodiment, taking an example where an audio device is an in-ear noise-canceling headphone, and the device has three MICs which are respectively FF, FB and Talk MICs, where the FF MIC is positioned outside an auditory meatus, and data obtained by the FF MIC is data of the external high-sound-pressure-level energy. Similarly, the data of the external high-sound-pressure-level energy may also be obtained by the Talk MIC.

In this embodiment, the preset first threshold represents the minimum energy that can be canceled when the system enables the ANC, and it is generally considered that the user's hearing will be impaired if no protective measure is taken within a reasonable time. In this embodiment, it is considered that the sound pressure energy level of the FF MIC, equivalent to the SPL of 80 dBA at the eardrum of the user belongs to the appropriate first threshold. The preset second threshold represents the maximum energy that can be canceled when the system enables the ANC. The high-sound-pressure-level energy, about to be saturated, of the FF MIC obtained by the laboratory test is the preset second threshold. When the high-sound-pressure-level energy exceeds the second threshold, the sound pressure level of the microphone with the ANC will be saturated to cause the ANC to fail. A speaker may output noise and even increase sound energy in the ear. At this time, the best protective measure is to disable the ANC and block the high-sound-pressure-level energy by only using the passive noise cancellation of the system.

For specific protective measures, in this embodiment, the system will compare the energy measured by the external microphone with the first threshold and the second threshold in real time, and take corresponding measures according to results. That is to say, when the energy of the microphone is higher than the first threshold and is lower than the second threshold, the system enables the ANC to avoid the high sound pressure level; and when the energy of the microphone is higher than the second threshold, the system disables the ANC to avoid the noise cancellation blockage failure caused by saturation of the sound pressure level of the microphone with the ANC.

Figure 3:
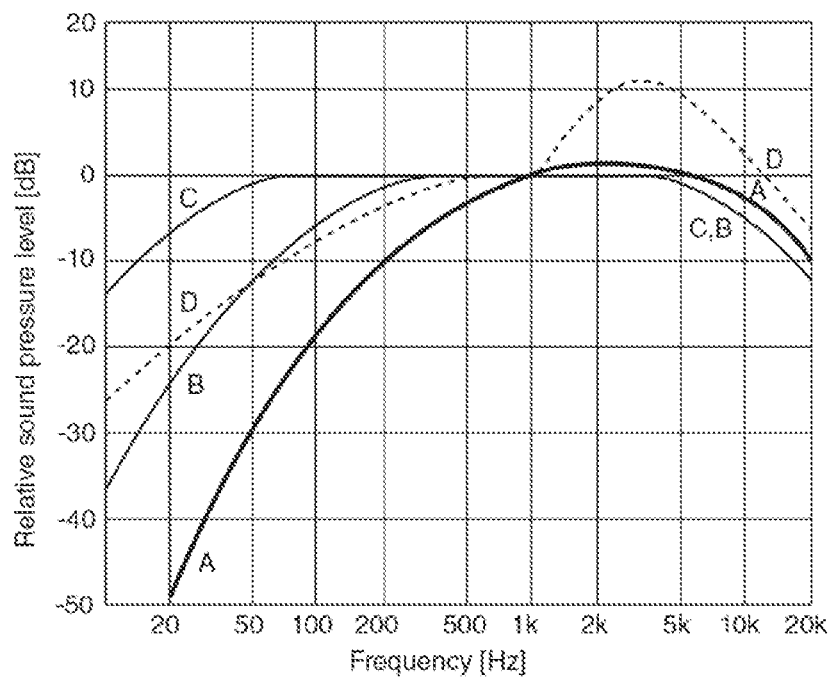
FIG. 3 is a schematic diagram of an A-weighted network curve.

On the basis of the above embodiment 1, for a method for measuring the external high sound pressure level, the audio device involved in the present disclosure can acquire the change of the external sound signal in real time by means of the external microphone, and convert the change of such sound signal into the audio data stream. The audio stream is calculated in an A-weighted mode to obtain the current sound energy. A-weighted is a standard weight curve for audio measurement, which is configured for reflecting the response characteristics of the human ears. The sound pressure level is derived from A-weighted and is denoted by dBA. A-weighted is widely used in the measurement of noise and stable audio signals, and its frequency domain curve is as shown in FIG. 3. It may be seen from FIG. 3 that when A-weighted is used for audio measurement, a weight of a low frequency will be lower than weights of medium and high frequencies. Because A-weighted is most meaningful for describing the frequency response of human ear's hearing relative to real acoustics, it is most widely used.

Specifically, a transfer function of the A-weighted digital system is as follows:

$$A(S) = 10^{\frac{-A_{1000}}{20}} \left[ \frac{\Omega_4^2 S^2}{(S^2 + \Omega_1^2)^2 (S^2 + \Omega_2^2)(S^2 + \Omega_3^2)(S^2 + \Omega_4^2)^2} \right],$$

where $\Omega_1 = 2\pi f_1, \Omega_2 = 2\pi f_2, \Omega_3 = 2\pi f_3, \Omega_4 = 2\pi f_4, A_{1000} = 1.9997,$ $f_1 = 20.60$ Hz, $f_2 = 107.7$ Hz, $f_3 = 737.9$ Hz, $f_4 = 12194$ Hz.

The transfer function of the A-weighted digital system is converted into a digital filter by means of MATLAB software, and a filter coefficient h(n) is obtained. Specifically, the transfer function of the A-weighted digital system is converted into the digital filter by means of bilinear transformation.

Figure 4:
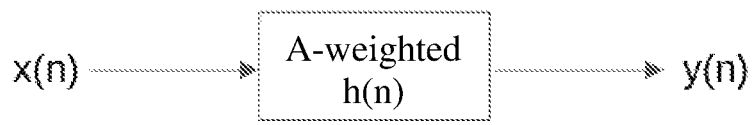
FIG. 4 is a schematic diagram of an architecture of the A-weighted digital system.

Referring to FIG. 4, if the input audio data stream is set as x(n), then y(n) is output after processing by the A-weighted digital system, and a sound pressure level of y(n) data is calculated to obtain a dBA value of a current audio, where a formula for calculating the sound pressure level is as follows:

$$SPL = 20 \times \log_{10} \frac{p_e}{p_{ref}},$$

where $$p_e = \sqrt{\frac{1}{N} \sum_{n=1}^{N} x^2(n)}, p_{ref=2\times 10^{-5}}.$$

The hearing protection method in the present disclosure may be controlled by arranging a virtual switch in practical application. For example, the virtual switch is correspondingly provided in the hearing protection method and is arranged in a preset application (App), the Step S1 to the Step S5 are performed when the virtual switch is turned on, and the Step S1 to the Step S5 are not performed when the virtual switch is turned off.

Compared with the prior art, the hearing protection method provided by the present disclosure has the following beneficial effects: the present disclosure can block the external high-sound-pressure-level energy, and can effectively protect hearing when the high-sound-pressure-level energy suddenly occurs outside, thereby better meeting application requirements.

The above is only the preferred embodiment of the present disclosure and is not intended to limit the present disclosure. Any modifications, equivalent substitutions or improvements made within the technical scope of the present disclosure shall be included in the scope of protection of the present disclosure.

What is claimed is:

1. A hearing protection method capable of blocking external high-sound-pressure-level energy, comprising the following steps:
    Step S1: presetting a first sound pressure energy threshold and a second sound pressure energy threshold, the second sound pressure energy threshold being greater than the first sound pressure energy threshold;
    Step S2: obtaining an external sound energy value;
    Step S3: comparing the external sound energy value with the first sound pressure energy threshold and the second sound pressure energy threshold, when the external sound energy value is greater than the first sound pressure energy threshold and is less than the second sound pressure energy threshold, performing Step S4, and when the external sound energy value is greater than the second sound pressure energy threshold, performing Step S5;
    Step S4: enabling a preset active noise cancellation function to reduce high-sound-pressure-level energy; and
    Step S5: disabling the preset active noise cancellation function, and blocking the high-sound-pressure-level energy by means of passive noise cancellation.

2. The hearing protection method capable of blocking external high-sound-pressure-level energy according to claim 1, wherein in the Step S1, a sound pressure energy level of a feed forward microphone (FF MIC), equivalent to a sound pressure level (SPL) of 80 dBA at an eardrum of a user, is taken as the first sound pressure energy threshold.

3. The hearing protection method capable of blocking external high-sound-pressure-level energy according to claim 1, wherein in the Step S1, a high sound pressure energy level, about to be saturated, of an FF MIC obtained by a laboratory test is taken as the second sound pressure energy threshold.

4. The hearing protection method capable of blocking external high-sound-pressure-level energy according to claim 1, wherein in the Step S2, the external sound energy value is obtained by an FF MIC or a Talk MIC.

5. The hearing protection method capable of blocking external high-sound-pressure-level energy according to claim 4, wherein in the Step S2, the process of obtaining the external sound energy value comprises: converting the change of an external sound signal acquired in real time by the FF MIC or the Talk MIC into an audio data stream, and calculating the audio data stream by means of an A-weighted digital system to obtain the current external sound energy value, wherein a transfer function of the A-weighted digital system is as follows:

$$A(S) = 10^{\frac{-A_{1000}}{20}} \left[ \frac{\Omega_4^2 S^2}{(S^2 + \Omega_1^2)^2 (S^2 + \Omega_2^2)(S^2 + \Omega_3^2)(S^2 + \Omega_4^2)^2} \right],$$

wherein $\Omega_1 = 2\pi f_1, \Omega_2 = 2\pi f_2, \Omega_3 = 2\pi f_3, \Omega_4 = 2\pi f_4, A_{1000} = 1.9997,$ $f_1 = 20.60$ Hz, $f_2 = 107.7$ Hz, $f_3 = 737.9$ Hz, $f_4 = 12194$ Hz;

converting the transfer function of the A-weighted digital system into a digital filter by means of MATLAB software, and obtaining a filter coefficient h(n); and if the input audio data stream is set as x(n), then outputting y(n) after processing by the A-weighted digital system, and calculating a sound pressure level of y(n) data to obtain a dBA value of a current audio, wherein a formula for calculating the sound pressure level is as follows:

$$SPL = 20 \times \log_{10} \frac{p_e}{p_{ref}},$$

wherein $$p_e = \sqrt{\frac{1}{N}\sum_{n=1}^{N} x^2(n)}, p_{ref=2 \times 10^{-5}}.$$

6. The hearing protection method capable of blocking external high-sound-pressure-level energy according to claim 5, wherein the transfer function of the A-weighted digital system is converted into the digital filter by means of bilinear transformation.

7. The hearing protection method capable of blocking external high-sound-pressure-level energy according to claim 1, wherein a virtual switch is correspondingly provided in the hearing protection method and is arranged in a preset application (App), the Step S1 to the Step S5 are performed when the virtual switch is turned on, and the Step S1 to the Step S5 are not performed when the virtual switch is turned off.

\* \* \* \* \*